(12) United States Patent
Voellmicke et al.

(10) Patent No.: US 9,833,334 B2
(45) Date of Patent: Dec. 5, 2017

(54) ENHANCED CAGE INSERTION ASSEMBLY

(71) Applicant: DePuy Synthes Products, Inc., Raynham, MA (US)

(72) Inventors: John C Voellmicke, Franklin, MA (US); Michael J O'Neil, West Barnstable, MA (US); Derek Shaw, North Attleboro, MA (US); Alexander Grinberg, Auburndale, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 43 days.

(21) Appl. No.: 14/623,982

(22) Filed: Feb. 17, 2015

(65) Prior Publication Data
US 2015/0157470 A1 Jun. 11, 2015

Related U.S. Application Data

(63) Continuation of application No. 12/822,739, filed on Jun. 24, 2010, now Pat. No. 8,979,860.

(51) Int. Cl.
*A61B 17/58* (2006.01)
*A61B 17/60* (2006.01)
(Continued)

(52) U.S. Cl.
CPC ............ *A61F 2/4455* (2013.01); *A61F 2/447* (2013.01); *A61F 2/4601* (2013.01); *A61F 2/4611* (2013.01); *A61F 2/446* (2013.01); *A61F 2/4465* (2013.01); *A61F 2002/30034* (2013.01); *A61F 2002/30092* (2013.01); *A61F 2002/30331* (2013.01); *A61F 2002/30604* (2013.01); *A61F 2002/30731* (2013.01);
(Continued)

(58) Field of Classification Search
CPC ... A61B 17/88; A61B 17/885; A61B 17/8875; A61B 17/8894; A61B 2017/90
USPC ............... 606/90, 96, 99, 104, 86 A; 623/17.11–17.16
See application file for complete search history.

(56) References Cited

U.S. PATENT DOCUMENTS

| 3,867,728 A | 2/1975 | Stubstad et al. |
| 4,349,921 A | 9/1982 | Kuntz |

(Continued)

FOREIGN PATENT DOCUMENTS

| CN | 101909548 A | 12/2010 |
| DE | 2804936 | 8/1979 |

(Continued)

OTHER PUBLICATIONS

Chiang, Biomechanical Comparison of Instrumented Posterior Lumbar Interbody Fusion with One or Two Cages by Finite Element Analysis, Spine, 2006, pp. E682-E689, vol. 31(19), Lippincott Williams & Wilkins, Inc.

(Continued)

*Primary Examiner* — Ellen C Hammond
*Assistant Examiner* — Christina Negrellirodrigue

(57) ABSTRACT

A method of delivering a fusion cage to an intervertebral disc space bounded by adjacent vertebral endplates, comprising the step of delivering the fusion cage into the disc space without contacting its teeth to the vertebral endplates during delivery, wherein a sheath is interposed between a cage surface and the endplates to prevent contact therebetween during delivery.

22 Claims, 12 Drawing Sheets

(51) Int. Cl.
  *A61F 2/00*  (2006.01)
  *A61F 2/44*  (2006.01)
  *A61F 2/46*  (2006.01)
  *A61F 2/30*  (2006.01)

(52) U.S. Cl.
  CPC . *A61F 2002/448* (2013.01); *A61F 2002/4475* (2013.01); *A61F 2310/00017* (2013.01); *A61F 2310/00023* (2013.01); *A61F 2310/00239* (2013.01)

(56) References Cited

U.S. PATENT DOCUMENTS

| | | |
|---|---|---|
| 4,743,256 A | 5/1988 | Brantigan |
| 4,759,766 A | 7/1988 | Buettner-Janz et al. |
| 4,863,476 A | 9/1989 | Shepperd |
| 4,871,366 A | 10/1989 | Von Recum et al. |
| 4,878,915 A | 11/1989 | Brantigan |
| 5,059,193 A | 10/1991 | Kuslich |
| 5,071,437 A | 12/1991 | Steffee |
| 5,123,926 A | 6/1992 | Pisharodi |
| 5,290,312 A | 3/1994 | Kojimoto et al. |
| 5,314,477 A | 5/1994 | Marnay |
| 5,344,252 A | 9/1994 | Kakimoto |
| 5,370,697 A | 12/1994 | Baumgartner |
| 5,390,683 A | 2/1995 | Pisharodi |
| 5,401,269 A | 3/1995 | Buttner-Janz et al. |
| 5,425,773 A | 6/1995 | Boyd et al. |
| 5,443,514 A | 8/1995 | Steffee |
| 5,507,816 A | 4/1996 | Bullivant |
| 5,522,899 A | 6/1996 | Michelson |
| 5,534,029 A | 7/1996 | Shima |
| 5,554,191 A | 9/1996 | Lahille et al. |
| 5,556,431 A | 9/1996 | Buttner-Janz |
| 5,562,738 A | 10/1996 | Boyd et al. |
| 5,609,635 A | 3/1997 | Michelson |
| 5,653,763 A | 8/1997 | Errico |
| 5,658,335 A | 8/1997 | Allen |
| 5,665,122 A | 9/1997 | Kambin |
| 5,676,701 A | 10/1997 | Yuan et al. |
| 5,683,465 A | 11/1997 | Shinn et al. |
| 5,697,977 A | 12/1997 | Pisharodi |
| 5,716,415 A | 2/1998 | Steffee |
| 5,772,661 A | 6/1998 | Michelson |
| 5,782,832 A | 7/1998 | Larsen et al. |
| 5,797,909 A | 8/1998 | Michelson |
| 5,860,973 A | 1/1999 | Michelson |
| 5,865,848 A | 2/1999 | Baker |
| 5,888,224 A | 3/1999 | Beckers et al. |
| 5,888,226 A | 3/1999 | Rogozinski |
| 5,888,227 A | 3/1999 | Cottle |
| 5,893,889 A | 4/1999 | Harrington |
| 5,893,890 A | 4/1999 | Pisharodi |
| 5,980,522 A | 11/1999 | Koros et al. |
| 5,989,291 A | 11/1999 | Ralph et al. |
| 6,039,761 A | 3/2000 | Li |
| 6,039,763 A | 3/2000 | Shelokov |
| 6,045,579 A | 4/2000 | Hochshuler |
| 6,080,155 A | 6/2000 | Michelson |
| 6,083,225 A * | 7/2000 | Winslow ............ A61B 17/025 606/279 |
| 6,096,038 A | 8/2000 | Michelson |
| 6,099,531 A | 8/2000 | Bonutti |
| 6,102,950 A | 8/2000 | Vaccaro |
| 6,106,557 A | 8/2000 | Robioneck et al. |
| 6,113,637 A | 9/2000 | Gill et al. |
| 6,113,638 A | 9/2000 | Williams et al. |
| 6,117,174 A | 9/2000 | Nolan |
| 6,127,597 A | 10/2000 | Beyar et al. |
| 6,129,763 A | 10/2000 | Chauvin et al. |
| 6,146,387 A | 11/2000 | Trott et al. |
| 6,176,882 B1 | 1/2001 | Biedermann et al. |
| 6,179,794 B1 | 1/2001 | Burras |
| 6,179,873 B1 | 1/2001 | Zientek |
| 6,183,517 B1 | 2/2001 | Suddaby |
| 6,193,757 B1 | 2/2001 | Foley et al. |
| 6,296,647 B1 | 10/2001 | Robioneck et al. |
| 6,302,914 B1 | 10/2001 | Michelson |
| 6,332,895 B1 | 12/2001 | Suddaby |
| 6,368,350 B1 | 4/2002 | Erickson et al. |
| 6,368,351 B1 | 4/2002 | Glenn |
| 6,375,682 B1 | 4/2002 | Fleischmann et al. |
| 6,387,130 B1 | 5/2002 | Stone |
| 6,409,766 B1 | 6/2002 | Brett |
| 6,419,705 B1 | 7/2002 | Erickson |
| 6,419,706 B1 | 7/2002 | Graf |
| 6,436,140 B1 | 8/2002 | Liu et al. |
| 6,454,806 B1 | 9/2002 | Cohen et al. |
| 6,454,807 B1 | 9/2002 | Jackson |
| 6,468,310 B1 | 10/2002 | Ralph et al. |
| 6,488,710 B2 | 12/2002 | Besselink |
| 6,517,580 B1 | 2/2003 | Ramadan et al. |
| 6,527,804 B1 | 3/2003 | Gauchet et al. |
| 6,533,818 B1 | 3/2003 | Weber et al. |
| 6,558,424 B2 | 5/2003 | Thalgott |
| 6,562,074 B2 | 5/2003 | Gerbec et al. |
| 6,582,468 B1 | 6/2003 | Gauchet |
| 6,610,094 B2 | 8/2003 | Husson |
| 6,641,614 B1 | 11/2003 | Wagner et al. |
| 6,648,917 B2 | 11/2003 | Gerbec et al. |
| 6,669,732 B2 | 12/2003 | Serhan et al. |
| 6,676,665 B2 | 1/2004 | Foley et al. |
| 6,706,070 B1 | 3/2004 | Wagner et al. |
| 6,719,796 B2 | 4/2004 | Cohen et al. |
| 6,723,126 B1 | 4/2004 | Berry |
| 6,733,532 B1 | 5/2004 | Gauchet et al. |
| 6,740,117 B2 | 5/2004 | Ralph et al. |
| 6,743,255 B2 | 6/2004 | Ferree |
| 6,773,460 B2 | 8/2004 | Jackson |
| 6,793,678 B2 | 9/2004 | Hawkins |
| 6,805,714 B2 | 10/2004 | Sutcliffe |
| 6,824,565 B2 | 11/2004 | Muhanna |
| 6,855,167 B2 | 2/2005 | Shimp |
| 6,863,673 B2 | 3/2005 | Gerbec et al. |
| 6,881,229 B2 | 4/2005 | Khandkar et al. |
| 6,893,464 B2 | 5/2005 | Kiester |
| 6,936,071 B1 | 8/2005 | Marnay et al. |
| 6,953,477 B2 | 10/2005 | Berry |
| 6,955,691 B2 | 10/2005 | Chae et al. |
| 6,969,404 B2 | 11/2005 | Ferree |
| 6,969,405 B2 | 11/2005 | Suddaby |
| 7,008,431 B2 | 3/2006 | Simonson |
| 7,018,412 B2 | 3/2006 | Ferreira et al. |
| 7,018,416 B2 | 3/2006 | Hanson et al. |
| 7,037,339 B2 | 5/2006 | Houfburg et al. |
| 7,083,650 B2 | 8/2006 | Moskowitz et al. |
| 7,094,257 B2 | 8/2006 | Mujwid et al. |
| 7,156,876 B2 | 1/2007 | Moumene et al. |
| 7,211,112 B2 | 5/2007 | Baynham et al. |
| 7,217,293 B2 | 5/2007 | Branch |
| 7,220,280 B2 | 5/2007 | Kast et al. |
| 7,223,292 B2 | 5/2007 | Messerli et al. |
| 7,226,483 B2 | 6/2007 | Gerber et al. |
| 7,235,101 B2 | 6/2007 | Berry et al. |
| 7,300,440 B2 | 11/2007 | Zdeblick |
| 7,326,248 B2 | 2/2008 | Michelson |
| 7,445,636 B2 * | 11/2008 | Michelson ............... A61F 2/446 606/249 |
| 7,503,933 B2 | 3/2009 | Michelson |
| 7,507,241 B2 | 3/2009 | Levy et al. |
| 7,517,363 B2 | 4/2009 | Rogers |
| 7,569,054 B2 | 8/2009 | Michelson |
| 7,569,074 B2 | 8/2009 | Eisermann et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,691,147 B2 | 4/2010 | Gutlin et al. |
| 7,703,727 B2 | 4/2010 | Selness |
| 7,722,612 B2 | 5/2010 | Sala et al. |
| 7,722,674 B1 | 5/2010 | Grotz |
| 7,749,270 B2 | 7/2010 | Peterman |
| 7,771,473 B2 | 8/2010 | Thramann |
| 7,785,368 B2 | 8/2010 | Schaller |
| 7,789,914 B2 | 9/2010 | Michelson |

(56) References Cited

U.S. PATENT DOCUMENTS

| | | |
|---|---|---|
| 7,799,083 B2 | 9/2010 | Smith et al. |
| 7,819,921 B2 | 10/2010 | Grotz |
| 7,824,445 B2 | 11/2010 | Biro et al. |
| 7,837,734 B2 | 11/2010 | Zucherman et al. |
| 7,846,206 B2 | 12/2010 | Oglaza et al. |
| 7,850,733 B2 | 12/2010 | Baynham et al. |
| 7,854,766 B2 | 12/2010 | Moskowitz et al. |
| 7,857,840 B2 | 12/2010 | Krebs |
| 7,874,980 B2 | 1/2011 | Sonnenschein et al. |
| 7,879,098 B1 | 2/2011 | Simmons |
| 7,887,589 B2 | 2/2011 | Glenn et al. |
| 7,909,870 B2 | 3/2011 | Kraus |
| 7,922,729 B2 | 4/2011 | Michelson |
| 7,951,199 B2 | 5/2011 | Miller |
| 7,985,231 B2 | 7/2011 | Sankaran |
| 7,993,403 B2 | 8/2011 | Foley et al. |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,043,381 B2 | 10/2011 | Hestad et al. |
| 8,062,375 B2 | 11/2011 | Glerum et al. |
| 8,075,621 B2 | 12/2011 | Michelson |
| 8,105,382 B2 | 1/2012 | Olmos et al. |
| 8,114,088 B2 | 2/2012 | Miller |
| 8,177,812 B2 | 5/2012 | Sankaran |
| 8,192,495 B2 | 6/2012 | Simpson et al. |
| 8,221,501 B2 | 7/2012 | Eisermann et al. |
| 8,221,502 B2 | 7/2012 | Branch |
| 8,231,681 B2 | 7/2012 | Castleman et al. |
| 8,236,058 B2 | 8/2012 | Fabian et al. |
| 8,241,358 B2 | 8/2012 | Butler et al. |
| 8,257,442 B2 | 9/2012 | Edie et al. |
| 8,262,666 B2 | 9/2012 | Baynham et al. |
| 8,267,939 B2 | 9/2012 | Cipoletti et al. |
| 8,273,128 B2 | 9/2012 | Oh et al. |
| 8,287,599 B2 | 10/2012 | McGuckin |
| 8,303,663 B2 | 11/2012 | Jimenez et al. |
| 8,323,345 B2 | 12/2012 | Sledge |
| 8,328,852 B2 | 12/2012 | Zehavi et al. |
| 8,337,559 B2 | 12/2012 | Hansell et al. |
| 8,353,961 B2 | 1/2013 | McClintock |
| 8,382,842 B2 | 2/2013 | Greenhalgh et al. |
| 8,398,713 B2 | 3/2013 | Weiman |
| 8,403,990 B2 | 3/2013 | Dryer et al. |
| 8,409,291 B2 | 4/2013 | Blackwell et al. |
| 8,435,298 B2 | 5/2013 | Weiman |
| 8,454,617 B2 | 6/2013 | Schaller |
| 8,486,148 B2 | 7/2013 | Butler et al. |
| 8,491,657 B2 | 7/2013 | Attia et al. |
| 8,491,659 B2 | 7/2013 | Weiman |
| 8,506,635 B2 | 8/2013 | Palmatier et al. |
| 8,518,087 B2 | 8/2013 | Palmatier et al. |
| 8,518,120 B2 | 8/2013 | Glerum et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim |
| 8,591,585 B2 | 11/2013 | McLaughlin et al. |
| 8,603,170 B2 | 12/2013 | Cipoletti et al. |
| 8,623,091 B2 | 1/2014 | Suedkamp et al. |
| 8,628,576 B2 | 1/2014 | Triplett et al. |
| 8,628,578 B2 | 1/2014 | Miller et al. |
| 8,632,595 B2 | 1/2014 | Weiman |
| 8,663,329 B2 | 3/2014 | Ernst |
| 8,668,740 B2 | 3/2014 | Rhoda et al. |
| 8,679,183 B2 | 3/2014 | Glerum et al. |
| 8,685,098 B2 | 4/2014 | Glerum et al. |
| 8,696,751 B2 | 4/2014 | Ashley et al. |
| 8,709,086 B2 | 4/2014 | Glerum et al. |
| 8,715,351 B1 | 5/2014 | Pinto |
| 8,721,723 B2 | 5/2014 | Hansell et al. |
| 8,728,160 B2 | 5/2014 | Globerman et al. |
| 8,753,398 B2 | 6/2014 | Gordon et al. |
| 8,771,360 B2 | 7/2014 | Jimenez et al. |
| 8,778,025 B2 | 7/2014 | Ragab et al. |
| 8,795,366 B2 | 8/2014 | Varela |
| 8,828,085 B1 | 9/2014 | Jensen |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,307 B2 | 12/2014 | Hawkins et al. |
| 8,926,704 B2 | 1/2015 | Glerum |
| 8,936,641 B2 | 1/2015 | Cain |
| 8,940,052 B2 | 1/2015 | Lechmann et al. |
| 8,979,860 B2 | 3/2015 | Voellmicke et al. |
| 9,039,771 B2 | 5/2015 | Glerum et al. |
| 9,091,488 B2 | 7/2015 | Malandain |
| 9,095,446 B2 | 8/2015 | Landry et al. |
| 9,095,447 B2 | 8/2015 | Barreiro et al. |
| 2002/0010070 A1 | 1/2002 | Cales et al. |
| 2002/0068976 A1 | 6/2002 | Jackson |
| 2002/0068977 A1 | 6/2002 | Jackson |
| 2002/0128715 A1 | 9/2002 | Bryan et al. |
| 2002/0128716 A1 | 9/2002 | Cohen et al. |
| 2002/0138146 A1 | 9/2002 | Jackson |
| 2002/0151976 A1 | 10/2002 | Foley et al. |
| 2002/0165612 A1 | 11/2002 | Gerber et al. |
| 2003/0004575 A1 | 1/2003 | Erickson |
| 2003/0004576 A1 | 1/2003 | Thalgott |
| 2003/0023305 A1 | 1/2003 | McKay |
| 2003/0040799 A1 | 2/2003 | Boyd et al. |
| 2003/0065396 A1 | 4/2003 | Michelson |
| 2003/0078667 A1 | 4/2003 | Manasas et al. |
| 2003/0130739 A1 | 7/2003 | Gerbec et al. |
| 2003/0135275 A1 | 7/2003 | Garcia |
| 2003/0139812 A1 | 7/2003 | Garcia |
| 2003/0139813 A1 | 7/2003 | Messerli et al. |
| 2003/0204261 A1 | 10/2003 | Eiserman |
| 2003/0233145 A1 | 12/2003 | Landry et al. |
| 2004/0030387 A1 | 2/2004 | Landry et al. |
| 2004/0064144 A1 | 4/2004 | Johnson et al. |
| 2004/0087947 A1 | 5/2004 | Lim |
| 2004/0088055 A1 | 5/2004 | Hanson et al. |
| 2004/0127991 A1 | 7/2004 | Ferree |
| 2004/0153065 A1 | 8/2004 | Lim |
| 2004/0153156 A1 | 8/2004 | Cohen et al. |
| 2004/0162618 A1 | 8/2004 | Mujwid et al. |
| 2004/0172133 A1 | 9/2004 | Gerber et al. |
| 2004/0186570 A1 | 9/2004 | Rapp |
| 2004/0186577 A1 | 9/2004 | Ferree |
| 2004/0230309 A1 | 11/2004 | DiMauro |
| 2005/0019365 A1 | 1/2005 | Frauchiger et al. |
| 2005/0038515 A1 | 2/2005 | Kunzler |
| 2005/0113916 A1 | 5/2005 | Branch |
| 2005/0113917 A1 | 5/2005 | Chae et al. |
| 2005/0125062 A1 | 6/2005 | Biedermann et al. |
| 2005/0165485 A1 | 7/2005 | Trieu |
| 2005/0222681 A1 | 10/2005 | Richley et al. |
| 2005/0256576 A1 | 11/2005 | Moskowitz et al. |
| 2005/0261769 A1 | 11/2005 | Moskowitz et al. |
| 2005/0278026 A1 | 12/2005 | Gordon et al. |
| 2006/0058876 A1 | 3/2006 | McKinley |
| 2006/0058880 A1 | 3/2006 | Wysocki |
| 2006/0100706 A1 | 5/2006 | Shadduck et al. |
| 2006/0122701 A1 | 6/2006 | Kiester |
| 2006/0122703 A1 | 6/2006 | Aebi et al. |
| 2006/0129244 A1 | 6/2006 | Ensign |
| 2006/0136062 A1 | 6/2006 | DiNello et al. |
| 2006/0142858 A1 | 6/2006 | Colleran et al. |
| 2006/0206207 A1 | 9/2006 | Dryer et al. |
| 2006/0235531 A1 | 10/2006 | Buettner |
| 2006/0253201 A1 | 11/2006 | McLuen |
| 2006/0265075 A1 | 11/2006 | Baumgartner et al. |
| 2006/0265077 A1 | 11/2006 | Zwirkoski |
| 2007/0010886 A1 | 1/2007 | Banick et al. |
| 2007/0055377 A1 | 3/2007 | Hanson et al. |
| 2007/0118222 A1 | 5/2007 | Lang |
| 2007/0149978 A1 | 6/2007 | Shezifi et al. |

(56) References Cited

U.S. PATENT DOCUMENTS

| | | |
|---|---|---|
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0191959 A1 | 8/2007 | Hartmann et al. |
| 2007/0198089 A1 | 8/2007 | Moskowitz et al. |
| 2007/0208423 A1 | 9/2007 | Messerli et al. |
| 2007/0219634 A1 | 9/2007 | Greenhalgh et al. |
| 2007/0233244 A1 | 10/2007 | Lopez et al. |
| 2007/0270968 A1 | 11/2007 | Baynham et al. |
| 2007/0276375 A1 | 11/2007 | Rapp |
| 2007/0299521 A1 | 12/2007 | Glenn |
| 2008/0009877 A1 | 1/2008 | Sankaran et al. |
| 2008/0015701 A1 | 1/2008 | Garcia et al. |
| 2008/0021556 A1 | 1/2008 | Edie |
| 2008/0021558 A1 | 1/2008 | Thramann |
| 2008/0027550 A1 | 1/2008 | Link et al. |
| 2008/0033440 A1 | 2/2008 | Moskowitz et al. |
| 2008/0058944 A1 | 3/2008 | Duplessis et al. |
| 2008/0065219 A1 | 3/2008 | Dye |
| 2008/0082173 A1 | 4/2008 | Delurio et al. |
| 2008/0132934 A1 | 6/2008 | Reiley |
| 2008/0140207 A1 | 6/2008 | Olmos |
| 2008/0147193 A1 | 6/2008 | Matthis et al. |
| 2008/0154377 A1 | 6/2008 | Voellmicke et al. |
| 2008/0161927 A1 | 7/2008 | Savage |
| 2008/0167657 A1 | 7/2008 | Greenhalgh |
| 2008/0177388 A1 | 7/2008 | Patterson et al. |
| 2008/0183204 A1 | 7/2008 | Greenhalgh et al. |
| 2008/0195209 A1 | 8/2008 | Garcia et al. |
| 2008/0243251 A1 | 10/2008 | Stad et al. |
| 2008/0243254 A1 | 10/2008 | Butler |
| 2008/0249622 A1 | 10/2008 | Gray |
| 2008/0281425 A1 | 11/2008 | Thalgott |
| 2009/0005873 A1 | 1/2009 | Slivka et al. |
| 2009/0030423 A1 | 1/2009 | Puno |
| 2009/0054991 A1 | 2/2009 | Biyani |
| 2009/0076610 A1 | 3/2009 | Afzal |
| 2009/0099568 A1 | 4/2009 | Lowry et al. |
| 2009/0105712 A1 | 4/2009 | Dauster |
| 2009/0112320 A1 | 4/2009 | Kraus |
| 2009/0112324 A1 | 4/2009 | Refai et al. |
| 2009/0164020 A1 | 6/2009 | Janowski |
| 2009/0177284 A1 | 7/2009 | Rogers et al. |
| 2009/0198339 A1 | 8/2009 | Kleiner |
| 2009/0222096 A1 | 9/2009 | Trieu |
| 2009/0222099 A1 | 9/2009 | Liu et al. |
| 2009/0234398 A1 | 9/2009 | Chirico et al. |
| 2009/0240335 A1 | 9/2009 | Arcenio et al. |
| 2009/0248159 A1 | 10/2009 | Aflatoon |
| 2009/0292361 A1 | 11/2009 | Lopez et al. |
| 2010/0016905 A1 | 1/2010 | Greenhalgh et al. |
| 2010/0069914 A1* | 3/2010 | Puno ................ A61F 2/4611 606/99 |
| 2010/0076559 A1 | 3/2010 | Bagga |
| 2010/0114105 A1 | 5/2010 | Butters |
| 2010/0179594 A1 | 7/2010 | Theofilos et al. |
| 2010/0204795 A1 | 8/2010 | Greenhalgh |
| 2010/0234956 A1 | 9/2010 | Attia et al. |
| 2010/0262240 A1 | 10/2010 | Chavatte et al. |
| 2010/0286783 A1 | 11/2010 | Lechmann et al. |
| 2010/0324607 A1 | 12/2010 | Davis |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0093074 A1 | 4/2011 | Glerum et al. |
| 2011/0130835 A1 | 6/2011 | Ashley et al. |
| 2011/0130838 A1 | 6/2011 | Morgenstern et al. |
| 2011/0144753 A1 | 6/2011 | Marchek et al. |
| 2011/0172716 A1 | 7/2011 | Glerum |
| 2011/0270261 A1 | 11/2011 | Mast et al. |
| 2011/0282453 A1 | 11/2011 | Greenhalgh et al. |
| 2011/0301711 A1 | 12/2011 | Palmatier et al. |
| 2011/0301712 A1 | 12/2011 | Palmatier et al. |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0071977 A1 | 3/2012 | Oglaza et al. |
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0185049 A1 | 7/2012 | Varela |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0310939 A1 | 11/2013 | Fabian et al. |
| 2014/0039622 A1 | 2/2014 | Glerum et al. |
| 2014/0046333 A1 | 2/2014 | Johnson et al. |
| 2014/0058513 A1 | 2/2014 | Gahman et al. |
| 2014/0067073 A1 | 3/2014 | Hauck |
| 2014/0114423 A1 | 4/2014 | Suedkamp et al. |
| 2014/0128977 A1 | 5/2014 | Glerum et al. |
| 2014/0135934 A1 | 5/2014 | Hansell et al. |
| 2014/0142706 A1 | 5/2014 | Hansell et al. |
| 2014/0163683 A1 | 6/2014 | Seifert et al. |
| 2014/0172106 A1 | 6/2014 | To et al. |
| 2014/0180421 A1 | 6/2014 | Glerum et al. |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0303731 A1 | 10/2014 | Glerum et al. |
| 2014/0303732 A1 | 10/2014 | Rhoda et al. |
| 2014/0324171 A1 | 10/2014 | Glerum et al. |
| 2015/0045894 A1 | 2/2015 | Hawkins et al. |
| 2015/0094812 A1 | 4/2015 | Marden et al. |
| 2015/0094813 A1 | 4/2015 | Lechmann et al. |
| 2015/0157470 A1 | 6/2015 | Voellmicke et al. |
| 2015/0173916 A1 | 6/2015 | Cain et al. |
| 2015/0216671 A1 | 8/2015 | Cain et al. |
| 2015/0216672 A1 | 8/2015 | Cain et al. |
| 2016/0317317 A1 | 11/2016 | Marchek et al. |

FOREIGN PATENT DOCUMENTS

| | | |
|---|---|---|
| DE | 3911610 | 10/1990 |
| DE | 4012622 | 7/1997 |
| DE | 202008001079 | 3/2008 |
| EP | 282161 | 9/1988 |
| EP | 678489 | 10/1995 |
| EP | 1290985 | 3/2003 |
| EP | 1532949 | 5/2005 |
| EP | 1541096 | 6/2005 |
| EP | 1683593 | 7/2006 |
| EP | 1698305 B1 | 8/2007 |
| EP | 1843723 B1 | 3/2010 |
| EP | 2368529 | 9/2011 |
| EP | 2237748 B1 | 9/2012 |
| EP | 2764851 | 8/2014 |
| FR | 2718635 | 10/1995 |
| FR | 2730159 | 8/1996 |
| FR | 2874814 | 3/2006 |
| JP | 2003-526457 | 9/2003 |
| JP | 2006-516456 | 7/2006 |
| JP | 2011-509766 A | 3/2011 |
| WO | WO 1994/004100 | 3/1994 |
| WO | WO 1995/031158 | 11/1995 |
| WO | WO 97/00054 | 1/1997 |
| WO | WO 1999/053871 | 10/1999 |
| WO | WO 2000/012033 | 3/2000 |
| WO | WO 2000/074605 | 12/2000 |
| WO | WO 01/01895 | 1/2001 |
| WO | WO 2000/53127 | 1/2001 |
| WO | WO 2001001893 | 1/2001 |
| WO | WO 2001/017464 | 3/2001 |
| WO | WO 2005/112834 | 12/2005 |
| WO | WO 2006/047587 | 5/2006 |

(56) References Cited

FOREIGN PATENT DOCUMENTS

| WO | WO 2006/058281 | 6/2006 |
|---|---|---|
| WO | WO 2006/065419 | 6/2006 |
| WO | WO 2006/081843 | 8/2006 |
| WO | WO 2007/028098 | 3/2007 |
| WO | WO 2007/048012 | 4/2007 |
| WO | WO 2008/044057 | 4/2008 |
| WO | WO 2007/009107 | 8/2008 |
| WO | WO 2009/092102 | 7/2009 |
| WO | WO 2009/064787 | 8/2009 |
| WO | WO 2009/124269 | 10/2009 |
| WO | WO 2009/143496 | 11/2009 |
| WO | WO 2010/068725 | 6/2010 |
| WO | WO 2010/148112 | 12/2010 |
| WO | WO 2011/142761 | 11/2011 |
| WO | WO 2012/009152 | 1/2012 |
| WO | WO 2012/089317 | 7/2012 |
| WO | WO 2012/135764 | 10/2012 |
| WO | WO 2013/006669 | 1/2013 |
| WO | WO 2013/023096 | 2/2013 |
| WO | WO 2013/025876 | 2/2013 |
| WO | WO 2013/043850 | 5/2013 |
| WO | WO 2013/062903 | 5/2013 |
| WO | WO 2013/082184 | 6/2013 |
| WO | WO 2013/158294 | 10/2013 |
| WO | WO 2013/173767 | 11/2013 |
| WO | WO 2013/184946 | 12/2013 |
| WO | WO 2014/018098 | 1/2014 |
| WO | WO 2014/026007 | 2/2014 |
| WO | WO 2014/035962 | 3/2014 |
| WO | WO 2014/088521 | 6/2014 |
| WO | WO 2014/116891 | 7/2014 |
| WO | WO 2014/144696 | 9/2014 |

OTHER PUBLICATIONS

Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Gore, Technique of Cervical Interbody Fusion, Clinical Orthopaedics and Related Research, 1984, pp. 191-195, No. 188.
Hunt, Expanable cage placement via a posterolateral approach in lumbar spine reconstructions, Journal of Neurosurgery: Spine, 2006, pp. 271-274, vol. 5.
Krbec, [Replacement of the vertebral body with an expansion implant (Synex)], Acta Chir Orthop Traumatol Cech, 2002, pp. 158-162, vol. 69(3).
Polikeit, The importance of the endplate for interbody cages in the lumbar spine, Eur Spine J, 2003, pp. 556-561, vol. 12.
Shin, Posterior Lumbar Interbody Fusion via a Unilateral Approach, Yonsei Medical Journal, 2006, pp. 319-325, vol. 47(3).
Hoogland, T. et al., Total Lumbar Intervertebral Disc Replacement: testing of a New Articulating Space in Human Cadaver Spines—24 1 Annual ORS, Dallas TX, Feb. 21-23, 1978, 8 pages.
Spine Solutions Brochure—Prodisc 2001, 16 pages.
Link SB Charite Brochure—Intervertebral Prosthesis 1988, 29 pages.

\* cited by examiner

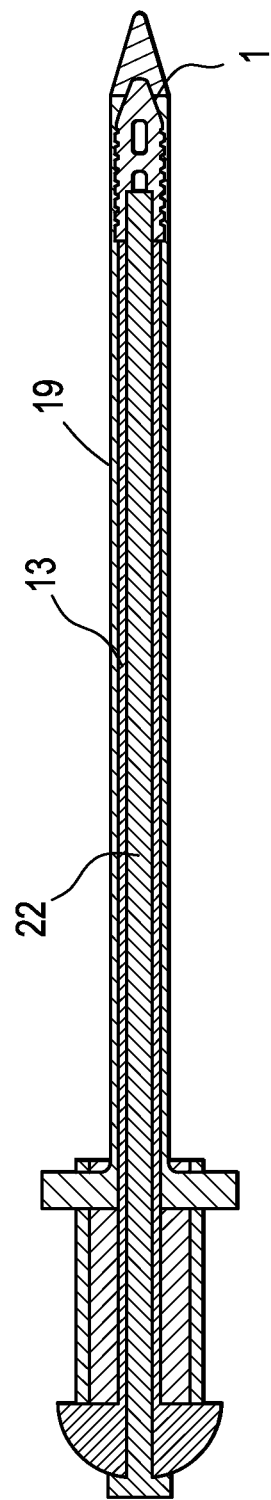

ENHANCED CAGE INSERTION ASSEMBLY

CONTINUING DATA

This application is a continuation of and claims priority from U.S. Ser. No. 12/822,739, filed Jun. 24, 2010, entitled "Enhanced Cage Insertion Device" (Voellmicke) (DEP6325USNP), the specification of which is incorporated by reference in its entirety.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus with its cushioning qualities. These nucleus pulposus cells may also secrete small amounts of cytokines as well as matrix metalloproteinases (MMPs). These cytokines and MMPs help regulate the metabolism of the nucleus pulposus cells.

In some instances of degenerative disc disease (DDD), gradual degeneration of the intervertebral disc is caused by mechanical instabilities in other portions of the spine. In these instances, increased loads and pressures on the nucleus pulposus cause the cells within the disc (or invading macrophages) to emit larger than normal amounts of the abovementioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of proinflammatory cytokines and/or MMPs that may cause nerve irritation and pain.

As DDD progresses, toxic levels of the cytokines and MMPs present in the nucleus pulposus begin to degrade the extracellular matrix. In particular, the MMPs (as mediated by the cytokines) begin cleaving the water-retaining portions of the proteoglycans, thereby reducing their water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, typically thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc and replace it with a porous device that restores disc height and allows for bone growth therethrough for the fusion of the adjacent vertebrae. These devices are commonly called "fusion devices".

Designs of intervertebral fusion devices are generally either box-like (i.e., Smith-Robinson style) or threaded cylinders (i.e., Cloward style). Smith-Robinson style implants have the advantage of possessing better contact area to the vertebral endplates, but rely on a coarse surface texture (such as teeth) to prevent their migration once implanted. Insertion then requires over distraction of the disc space to slide the implant in or to provide a smoother implant, which can migrate post-op.

One such box-like design is the Brantigan cage, which is disclosed in U.S. Pat. No. 4,743,256 ("Brantigan"). Brantigan discloses an improved surgical method for eliminating spinal back pain caused by ruptured or degenerated vertebral discs by spanning the disc space between adjacent vertebrae with rigid fusion devices, or "cages", having surfaces facilitating bone ingrowth and bottomed on prepared sites of the vertebrae to integrate the implant with the vertebrae and to provide a permanent weight supporting strut maintaining the disc space.

One commercial box-like design is the injection-molded carbon fiber reinforced PEEK (CFRP) cage made by DePuy Spine. However, these cages are difficult to insert because of the interference fit that is required for intervertebral space distraction. In addition, the reinforced PEEK material that makes up the teeth is brittle and so is susceptible to breakage when applying impact or torque loads to the implant.

Current interbody devices are made from single materials (e.g., machined titanium, or molded and/or machined PEEK). Titanium has the disadvantage of being radiopaque (which can interfere with fusion assessment on x-ray) while also having a high modulus of elasticity (which can stress shield the bone graft). Injection molded CFRP is very brittle and susceptible to fracture during insertion. Unreinforced PEEK is much less brittle but also weaker than carbon-filled PEEK, requiring thicker-walled designs (diminishing space for bone graft). In addition, the teeth of an unreinforced PEEK cage are softer and so may allow more migration. Both PEEK and carbon-filled PEEK are radiolucent.

U.S. Pat. No. 6,824,565 ("Muhana") discloses implant and instrument designs wherein some of the implant embodiments have planked designs and a mating inserter instrument. However, the disclosed inserter wraps around the exterior of the implant and partially into grooves on the implant. Moreover, the disclosed implant is derived from bone and is not hollow. The insertion technique disclosed by Muhana requires a cutting tool to prepare a channel for the implant.

US Patent Publication 2008-0154377 (Voellmicke) discloses a cage adapted to contain an inserter within its inner volume during insertion.

US Patent Publication 2009-0198339 (Kleiner) discloses an implantable intervertebral fusion cage including a removable means for retaining material inside of the cage during implantation. Embodiments are directed toward an implantable intervertebral fusion cage that includes at least one removable shield or veneer that is capable of retaining a surgically useful material, such as a spinal fusion-inducing material, inside of the fusion cage during implantation and/or until the shield or veneer is removed. None of the Kleiner shields cover the teeth of the cages.

U.S. Pat. No. 7,569,054 (Michelson) discloses disc space docking and distraction means. In particular, Michelson discloses an apparatus for use in human surgery has a tubular member with a passage for providing protected access to a surgical site. The passage has a minimum width transverse to the mid-longitudinal axis of the tubular member. Two opposed extensions extend from the distal end of the tubular member. The extensions each have a length and a maximum height perpendicular to the length. The maximum height of the extensions are less than the length of each extension and greater than one-half the minimum width of the passage. Each extension has an interior surface at least in part facing the mid-longitudinal axis of the tubular member. The interior surfaces of the extensions are spaced apart from one another along the length of each extension a distance no less than the minimum width of the passage. Each extension has opposed bone contacting surfaces configured to contact portions of bone.

Other relevant instruments include those disclosed in U.S. Pat. No. 7,008,431 ("Simonson"); U.S. Pat. No. 5,797,909 ("Michelson II"); U.S. Pat. No. 6,080,155 ("Michelson III"); U.S. Pat. No. 6,096,038 ("Michelson IV"); U.S. Pat. No. 7,300,440 ("Zdeblick"); and U.S. Patent Publication 2009-0198339 ("Kleiner").

In summary, the insertion of both smooth and toothed intervertebral cages has proven to be problematic due to high resistance forces (friction) and interference fit of the cage and intervertebral space. Whereas toothed cages are difficult to insert, cages with smooth upper and lower surfaces have demonstrated undesirable migration.

Current injection-molded PEEK or carbon fiber reinforced PEEK (CFRP) cages are difficult to insert because of the interference fit between the textured/spiked surfaces of the implant and the bony endplates.

The difficulty of direct, unshielded cage insertion and final positioning in the disc space also increases the likelihood of bony endplate damage, as the disc space preparation, FSU distraction forces and insertion trajectory are variable.

Consistent and accurate placement of the posteriorly inserted spinal fusion cages is difficult because light tamping and impaction are employed for final positioning. Cages have been over inserted via pushing or impaction through the annulus and into the adjacent body cavities and/or structures.

Most cages are filled with graft and/or bone inducing substances including BMP and collagen sponge. It has been found that the graft and/or BMP frequently drips or falls out of the graft retaining pockets. The uncontrolled delivery of the BMP/graft can irritate adjacent tissues and prompt bone formation in undesired locations including heterotopic bone.

Many spinal fusion procedures require either pre and or post packing of the disc space, thereby increasing patient risk and operative time.

SUMMARY OF THE INVENTION

In accordance with the present invention, there is provided a cage insertion instrument adapted to insert an intervertebral interbody cage through a conventional spinal surgery approach (such as ALIF, TLIF, PLIF, or LLIF). In preferred embodiments, this instrument includes a cannulated sheath comprising a) a proximal cannulated portion, and b) a distal cannulated sheath that surrounds the cage during insertion into the disc space. The sheath shields the textured surface of the cage from the vertebral body endplates, thereby preventing their stress-inducing engagement therewith. The sheath has an expandable tapered or bulleted distal tip to ease insertion and placement of the instrument (and cage) within the disc space. Once the cage is inserted to its proper depth in the disc space, the sheath can be refracted while the cage is held stationary by a threaded rod disposed within the sheath. This retraction exposes the sharp, textured surface of the cage for engagement with the vertebral endplates.

Therefore, the inserter of the present invention provides a number of benefits to the spinal surgeon. In particular, it provides initial distraction of the disc space, improves the ease of insertion and placement of an intervertebral spacer, minimizes damage to the spacer and/or endplate during spacer insertion and placement, provides a means to deliver and contain graft within the spacer and surrounding disc space, and reduces the secondary positioning and time required to implant a spacer.

The sheath also provides a delivery and containment means for bone graft and/or BMP's, bone graft can be placed either within the cage, or distal or proximal to the cage for simultaneous delivery therewith. This containment means prevents leakage during insertion into the body, during placement into the disc space, and during final deployment into the disc space.

Therefore, in accordance with the present invention, there is provided an assembly comprising:
a) an intervertebral fusion cage having a leading end, a trailing end, an upper face and a lower face, and
b) an inserter comprising:
   i) a cannulated rod holder having a bore therethrough,
   ii) a rod received within the bore of the cannulated rod holder, the rod adapted to mate with the cage,
   iii) a cannulated sheath receiving the cannulated rod holder, the sheath having a plurality of sheath portions extending distally therefrom, and
wherein a first sheath portion has an inner portion bearing against the lower face of the cage, and
wherein a second sheath portion has an inner portion bearing against the upper face of the cage.

The present invention includes a retractable sheath that holds a cage as it is inserted into the disc space, thereby shielding the sharp teeth of the cage from boney endplates and delivering graft to the disc space. Whereas conventional instrument systems that use delivery tubes for the cage do not place the tube into the disc space (but rather between the skin and the entrance to the disc space), the tubular sheath of the present invention enters the disc space.

The present invention also includes tubular, expandable spinal disc graft containment means.

Also in accordance with the present invention, there is provided a method of delivering a fusion cage to an intervertebral disc space bounded by adjacent vertebral endplates, comprising the step of:
a) delivering the fusion cage into the disc space without contacting its surfaces to the vertebral endplates during delivery.

In preferred embodiments thereof, a sheath is interposed between the cage surfaces and the endplates to prevent contact therebetween during delivery.

Also in accordance with the present invention, there is provided a method of delivering a fusion cage into the disc space, comprising the steps of:
a) inserting a distal end of a cannula into an intervertebral disc space,
b) delivering the fusion cage through the cannula into the disc space.

DESCRIPTION OF THE FIGURES

FIG. 5 discloses an inserter of the present invention having three main components.

DETAILED DESCRIPTION OF THE INVENTION

Figure 1A:
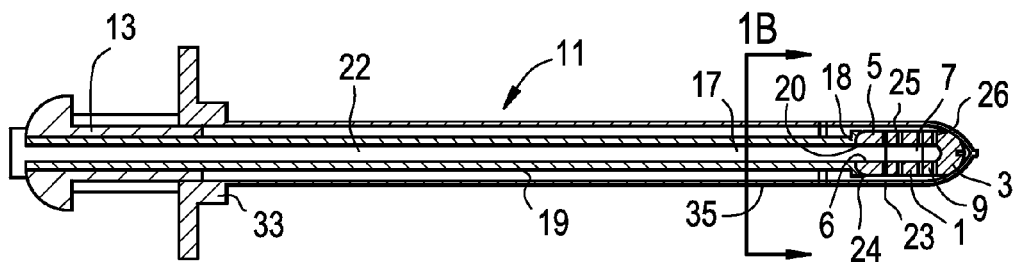
FIGS. 1A-1D disclose various views of an inserter of the present invention having four main components.
Figure 1B:
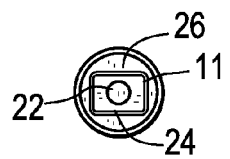
Figure 1C:
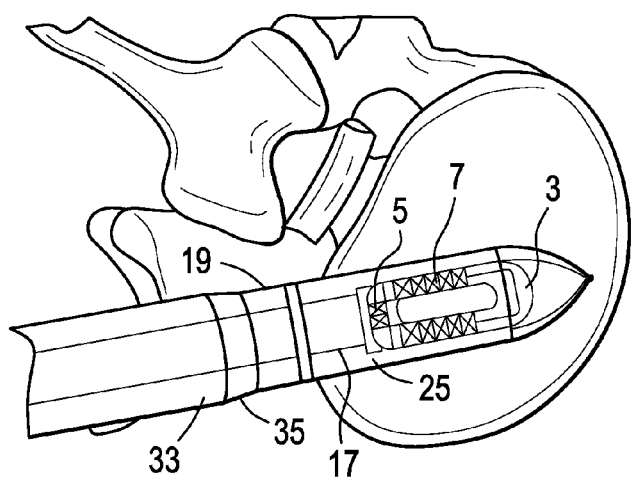
Figure 1D:
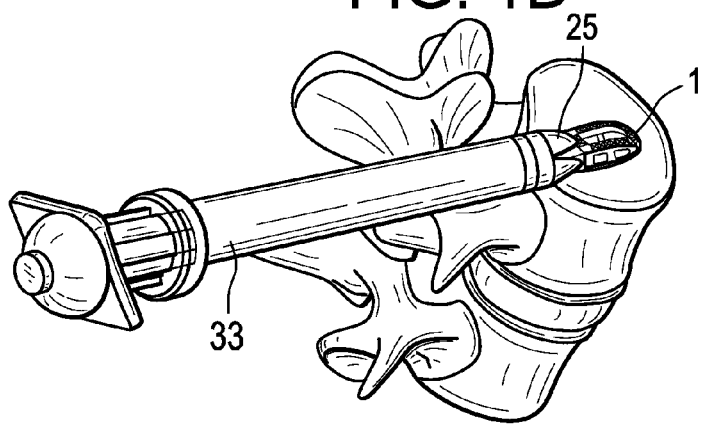

In some embodiments, the instrument comprises two, three, four or more components.

Now referring to FIGS. 1A-1D, there is provided an assembly of the present invention in which the inserter has four components: a sheath, a cannulated rod holder, a rod and a docking port. In particular, the assembly comprises:
- a) an intervertebral fusion cage 1 having a leading end 3, a trailing end 5 having a threaded hole 6, an upper face 7 and a lower face 9, and
- b) an inserter 11 comprising:
  - i) a cannulated rod holder 13 having a bore therethrough and a distal end portion 17 having a distal end 18 bearing against the trailing end of the cage,
  - ii) a rod 22 received within the bore of the cannulated rod holder, the rod having a threaded distal end 20 mating with the threaded hole of the cage,
  - iii) a cannulated sheath 19 adapted to receive the cannulated rod holder, the sheath having a plurality of sheath portions 23,25 extending distally therefrom,
  - iv) a docking port 33 having a bore therethrough and a substantially frustoconical distal end 35, wherein the cannulated sheath is slidingly received in the docking port and wherein a first sheath portion 23 has an inner portion 24 bearing against the lower face of the cage, and
wherein a second sheath portion 25 has an inner portion 26 bearing against the upper face of the cage.

In general, the rod is a proximally-handled instrument that mates with the cage and typically has a distally extending screw thread similar to conventional posterior cage inserters. It is typically called a threaded securement rod. Typically, the rod has a threaded distal end, the trailing end of the cage has a mating threaded hole, and the threaded distal end of the rod is received in the mating threaded hole of the cage to secure the cage. The threaded connection allows the surgeon to keep the cage in its inserted position while the sheath is removed therefrom.

Figure 2:
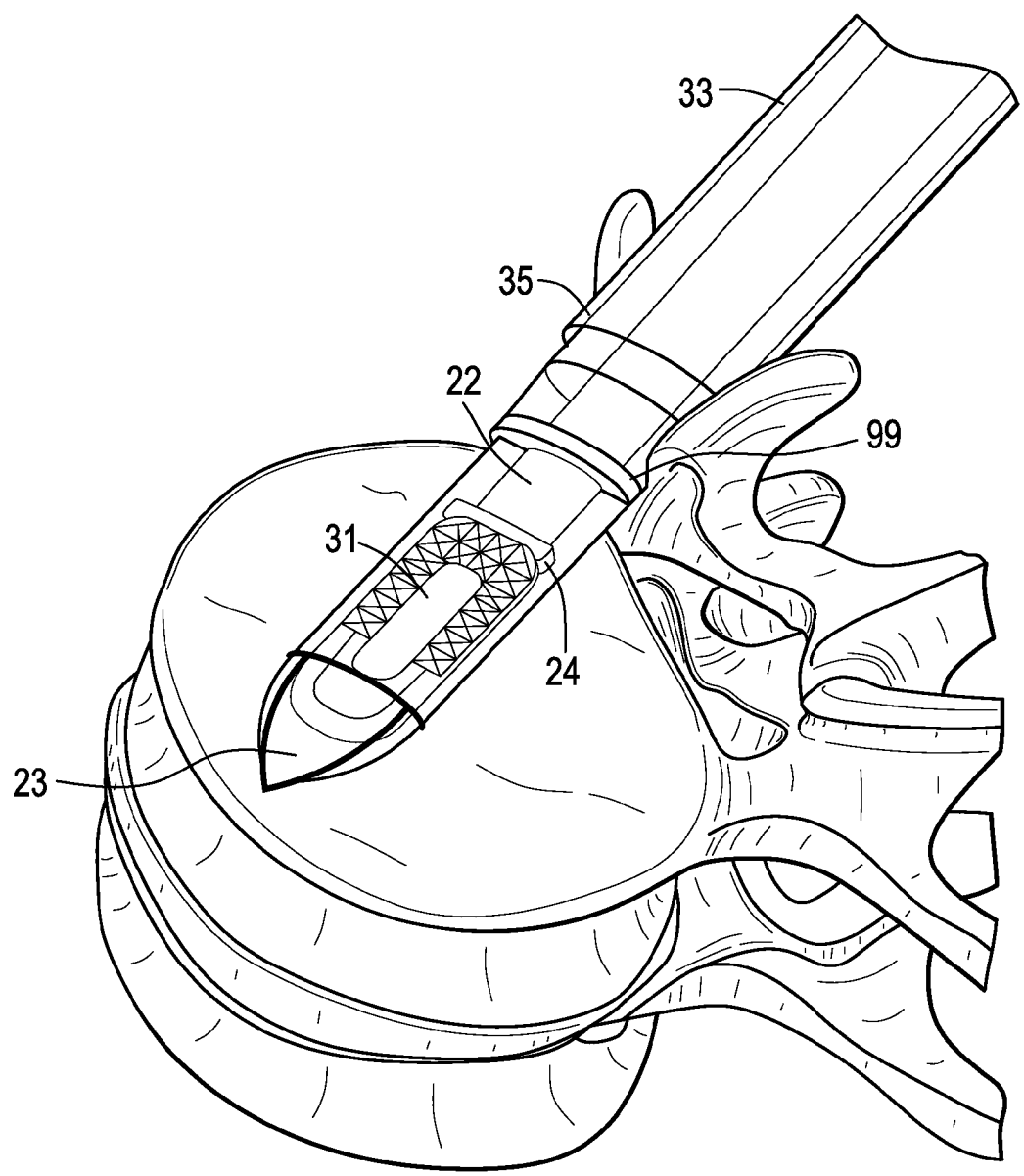
FIG. 2 discloses a fusion cage being held by an inserter of the present invention, along with the space available therein for graft placement.
Figure 3A:
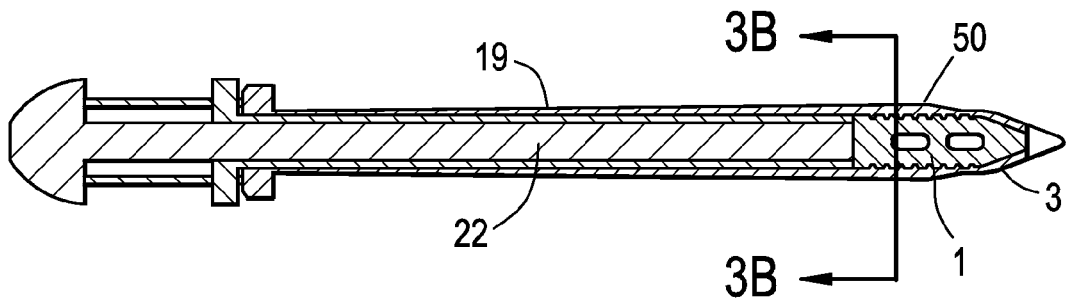
FIGS. 3A-3D disclose various views of an inserter of the present invention, wherein the sheath has a rectangular cross-section that tracks the cross-section of the fusion cage.
Figure 3B:
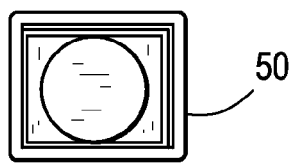
Figure 3C:
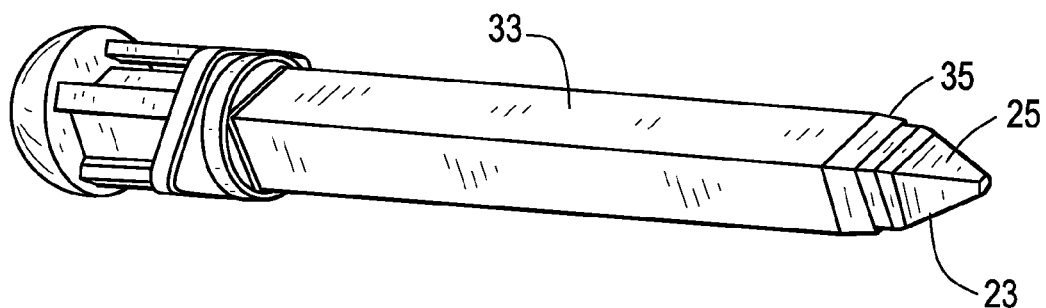
Figure 3D:
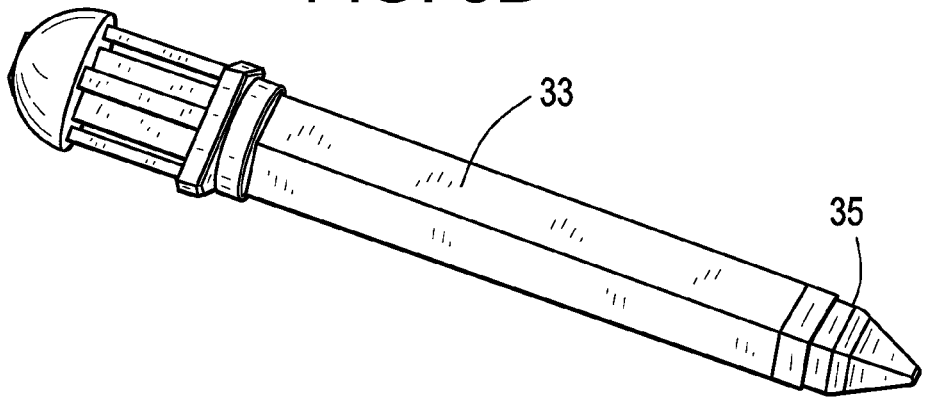
Figure 4A:
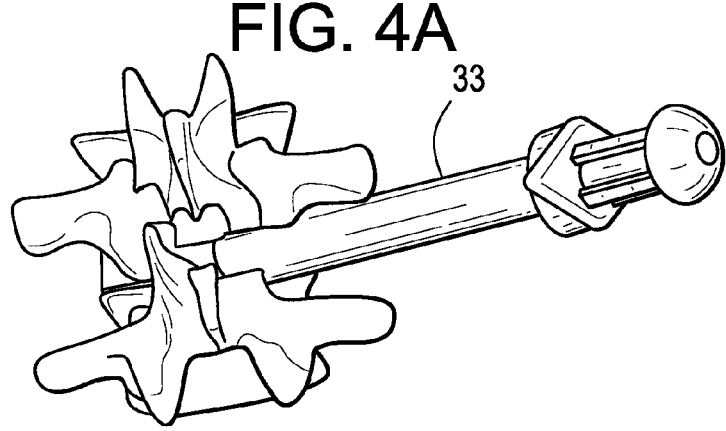
FIGS. 4A-4D disclose various steps by which the inserter of FIGS. 3A-3D inserts a cage into a disc space.
Figure 4B:
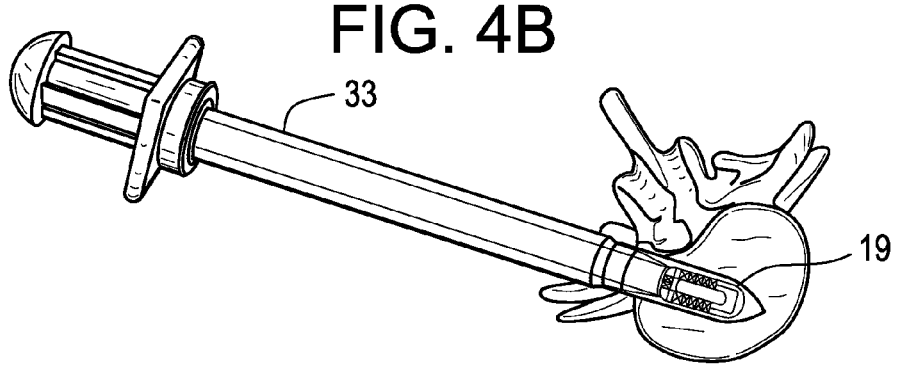
Figure 4C:
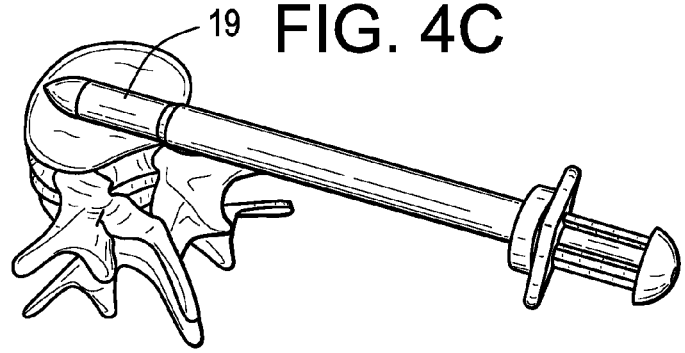
Figure 4D:
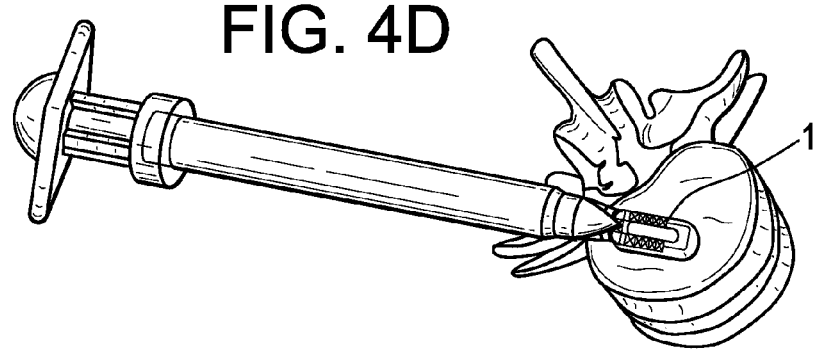

The function of the cannulated rod holder is to hold cage in position as sheath is retracted. As shown in FIG. 2, it typically has distally extending feet 24 for bearing against the trailing end of the cage. Thus, in some embodiments, the cannulated rod holder may be considered a cannulated cage holder as well. In some embodiments, the cannulated rod holder can further include a cylindrical flange or "piston" 99 that extends radially about the distal portion of the rod. This piston allows for sealed graft or BMP delivery distally thereof. As shown in FIG. 2, graft materials 31 can be placed within the cage, or placed distal and/or proximal to the cage within the cage holder, thereby eliminating the need to pre-pack or post-pack the disc space with graft materials. The piston feature provides a proximal stop for such graft placement proximal of the cage.

Referring back to FIGS. 1A-1D, the bulleted sheath 19 is a retractable cannulated sheath that slides over the rod/rod holder assembly. The sheath preferably has a very smooth (i.e., low coefficient of friction), semi-rigid inner wall 24,26 with a wall thickness of approximately 0.5 mm or less. Preferred materials of construction for the sheath include: polymerics (such as polyethylene, polypropylene, PEEK, polyurethane, and PTFE) or metallics (such as stainless steel, titanium alloy, and nitinol). One preferred sheath is constructed of a radiolucent material that allows for fluoroscopic imaging of the cage. In some embodiments, the sheath has a bulleted distal tip that optionally possesses at least one expansion slot (with four such slots shown in FIGS. 1A-1D, 2 and 4A-4D). Now referring to FIGS. 3A-3D, in some embodiments, the sheath can be produced in varying shapes, including those having a rectangular transverse cross-section 50.

In use, and now referring to FIG. 2, the sheath typically contains bone graft 31. In some cases, at least a portion of the bone graft is located within the cage. In others, at least a portion of the bone graft is located outside of the cage.

In some embodiments, the sheath comprises a distal pair of cup-like, opposed sheath half leafs, while in others the sheath comprises four sheath quarter leafs. Now referring to FIGS. 6A-6B, the proximal portion 98 of each distal sheath leaf 23, 25 is adapted to flex, thereby allowing the distal tip of the distal sheath leaf to open and close. In preferred embodiments, in their collapsed arrangement, the distal sheath leaves form a substantially conical shape distally, thereby forming a distal bullet tip. In other cases, the distal sheath leaves form a substantially tubular sheath shape proximally. In this way, the collective shape of the distal sheath leaves is much like that of a bulleted cage—i.e., it has a tubular body and a bulleted distal tip.

The distal sheath portions can also possess smooth outer surfaces to reduce friction and thereby increase the ease of insertion.

Typically, and now referring to FIG. 3A-3D, the inserter further comprises: iv) a docking port 33 having a bore therethrough and a substantially frustoconical distal end 35, wherein the cannulated sheath is slidingly received in the docking port. The docking port acts as a refractor for soft tissue and helps to place the cannulated sheath upon the vertebral body or within the disc. The docking port can also control insertion angle and depth of the bulleted sheath with enclosed cage. In some embodiments, the port is a cannulated body having a throughbore and a distal end portion having a tapered, cannulated, pyramidal or frustoconical shape.

The present invention is believed to be compatible with any conventional fusion cage. Typically, the upper and lower faces of the cage comprise a plurality of teeth. In some embodiments, the cage has a substantially rectangular transverse cross-section and the sheath has a corresponding substantially rectangular transverse cross-section. In some embodiments, the cage has a substantially circular transverse cross-section and the sheath has a corresponding substantially circular transverse cross-section. In some embodiments, the cage has a substantially elliptical transverse cross-section and the sheath has a corresponding substantially elliptical transverse cross-section.

Typically, the cage distracts the disc space during insertion. It is easy to insert and optimizes clinical performance once in place because it resists migration and subsidence, has an appropriate stiffness for load sharing, is preferably radiolucent, and has a shape that is able to contain injected graft material such as growth factors. In addition, the cage is robust over a wide variation of surgical technique because it will not break even when large forces are applied thereto.

The cage of the present invention is preferably compatible with the broad use of injectable paste-like bone grafting materials, such as BMP-containing pastes. It may be inserted empty and then filled with graft in-situ. With the availability of injectable pastes, cages will no longer require large, contiguous internal volumes to accept morselized/granular bone graft. Spaces can be smaller and more numerous. The cage of the present invention will be contained and shielded by the bulleted sheath and will therefore not experience as large impact loads during insertion.

Now referring to FIGS. 3A-3D, in some embodiments, the cage has a transverse cross-section 50 that is rectangular, and the transverse cross sections of the port, the bulleted sheath and the cannulated cage holder can substantially match that of the cage itself. This is a preferred embodiment, as it minimizes the over-distraction required in other embodiments for cage insertion.

Now referring to FIGS. 4A-4D, in one method of using the four-component inserter with the present invention, the sequence of implantation steps are as follows:

(1) fill the cage and sheath with bone graft.
(2) dock the docking port 33 onto the disc space. The port can be used to direct the angle and location of any desired disc clearing effort as well as cage implantation.
(3) advance of the bulleted sheath. The bulleted sheath 19 containing the graft and cage are advanced to the desired depth and location. The bulleted sheath reduces insertion forces due to its shape and its lubricious material of construction, while encasing the cage and its associated securement features (teeth).
(4) imaging. Imaging is performed to confirm cage positioning.
(5) sheath refraction: The sheath is retracted from the cage 1, thereby exposing the cage and its contents to the vertebral endplates.
(6) Cage Disconnection/Release: Following retraction of the sheath, the threaded rod is disengaged from the cage, thereby leaving the cage in the disc space at the desired location.
(7) Added Graft Injection (optional): As a last step, additional graft can be deployed via packing or injecting through the cannulated cage holder.

Now referring to FIG. 5, in some embodiments, the inserter instrument of the present invention is a three-component design that does not have a docking port. This design includes:

a) a threaded securement rod 23 that mates with the cage via screw threads in a manner similar to conventional posterior cage inserters;
b) a cannulated cage holder 13 to receive the rod and hold the cage in position as the sheath is retracted; and
c) a bulleted cannulated sheath 19.

In using the inserter of FIG. 5, the bulleted sheath (containing the graft and the cage 1) is advanced to the desired location. Due to the shape and lubricious material which encases the cage and associated securement features (such as teeth), the bulleted sheath reduces insertion forces. Imaging is then performed to confirm positioning.

Figure 6A:
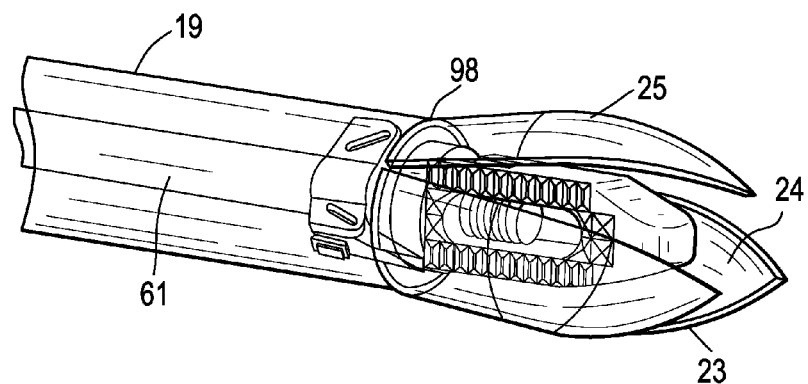
FIGS. 6A-6B discloses an inserter of the present invention having two main components.
Figure 6B:
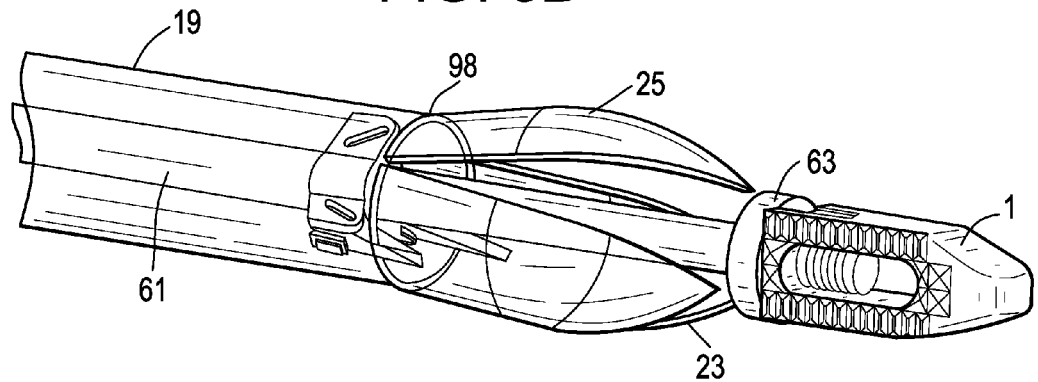

Now referring to FIGS. 6A-6B, there is provided a simple two-component embodiment of the present invention employing a cage pusher/holder 61 and an insertion sheath 19. The cage pusher/holder features the threaded feature of the rod and the shoulder 63 of the cannulated rod holder of FIGS. 1A-1D. The cage pusher/holder holds the cage 1 in position as sheath is retracted, and the feet can act as a piston for sealed graft delivery. The bulleted sheath 19 (containing the graft and cage) is advanced to the desired location. The bulleted sheath reduces insertion forces due to the shape and lubricious material which encases the cage and associated securement features (such as teeth). Imaging is performed to confirm positioning.

Figure 7A:
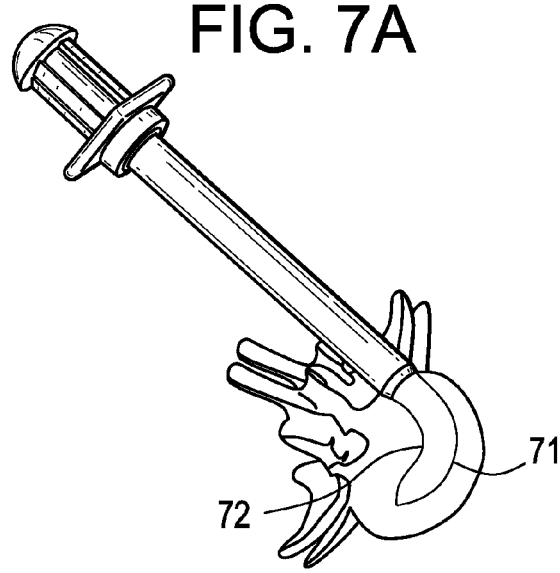
FIGS. 7A-7B discloses an inserter of the present invention having a curved distal sheath.
Figure 7B:
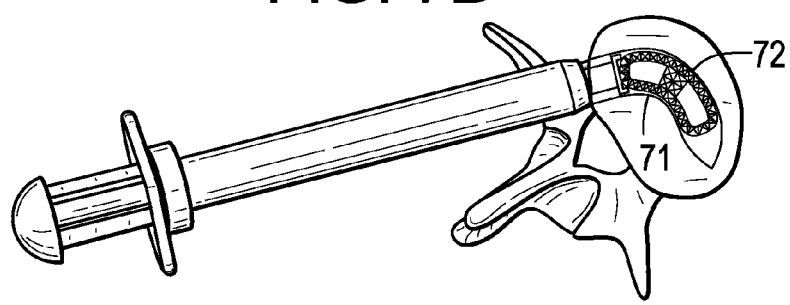

In some embodiments, and now referring to FIGS. 7A and 7B, the cages of the assembly of the present invention have curved sidewalls. Typically, these curved cages are placed in an anterior portion of the disc space. The curved sheath reduced the need for post-insertion manipulation of theses cages with conventional insertion methods which is more challenging due to the final position of the cage and the increased manipulation and forces that are required to push it in.

Figure 7C:
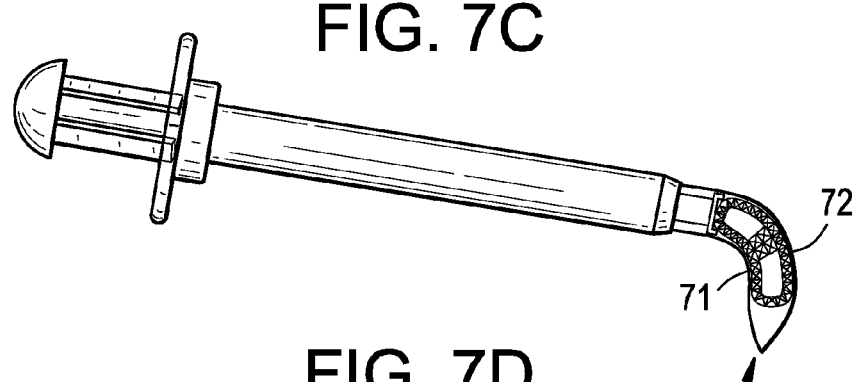
FIGS. 7C-7D discloses the distal and proximal loading of the inserter of FIGS. 7A-7B.
Figure 7D:
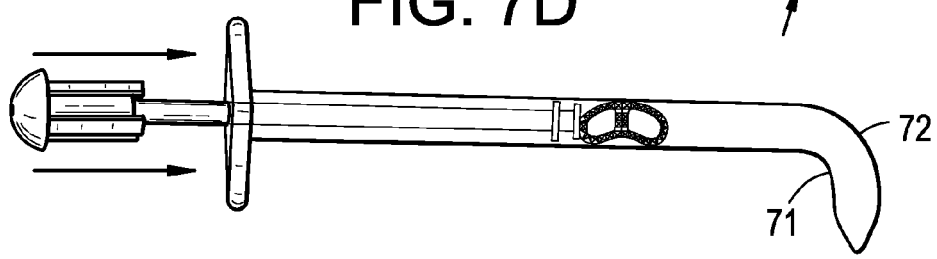
Figure 8A:
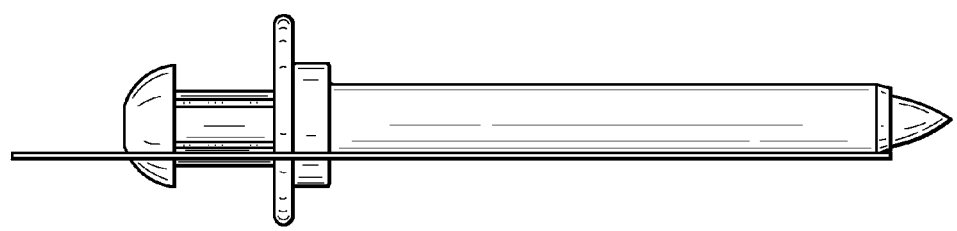
FIGS. 8A-8D disclose the sequential advance of the curved distal sheath of an inserter of the present invention.
Figure 8B:
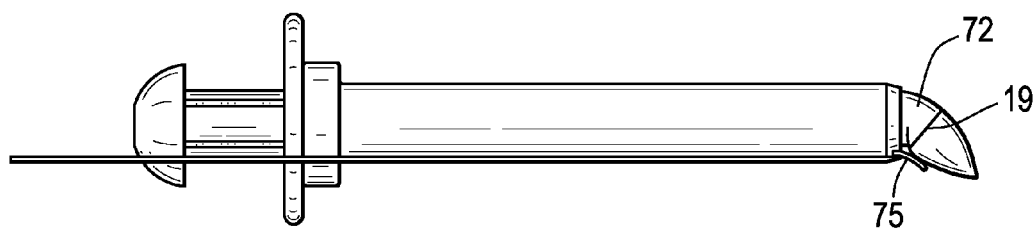
Figure 8C:
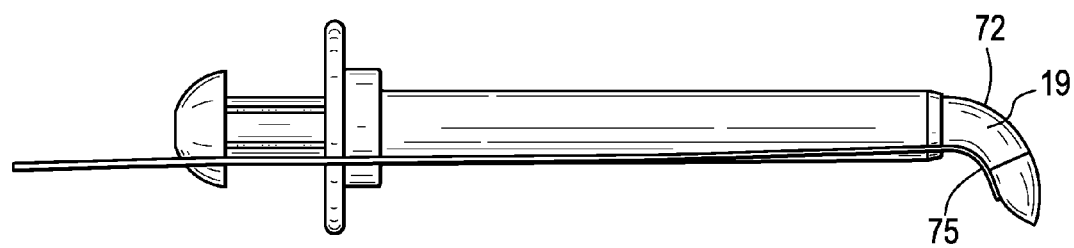
Figure 8D:
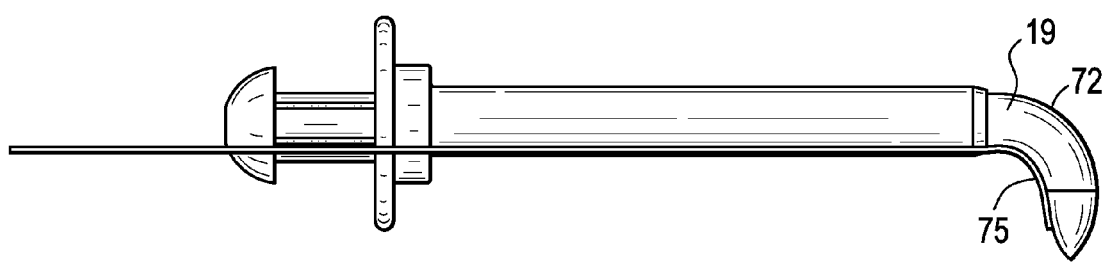

In preferred cases, the sheath is curved to help deliver these curved implants. In cases in which the sheath is curved, the sheath preferably comprises a superelastic shape memory material and has a curved configuration and a straight configuration. The sheath of the insertion device of the present invention also possesses curved sidewalls 71,72, thereby providing for shielded placement of the curved cage in the desired final location prior to sheath retraction. In one type of preferred curved inserter device (FIG. 7C), there is distal loading of the cage, allowing for minimal diameter of the bulleted sheath and cannulated cage holder. The second type of curved inserter device (FIG. 7D) allows for proximal cage loading, but requires an increased diameter of the bulleted sheath and cannulated cage holder. Such a curved inserter can be made to be self-steerable by using a memory metal or memory polymer sheath, or by using a threaded inserter that recovers its unloaded position upon deployment from the docking port.

In some embodiments, and now referring to FIGS. 8A-8D, the cage inserter can be steered into its desired location via cables or other means, wherein the sheath 19 has a tensioning cable 75 attached thereto.

Figure 9:
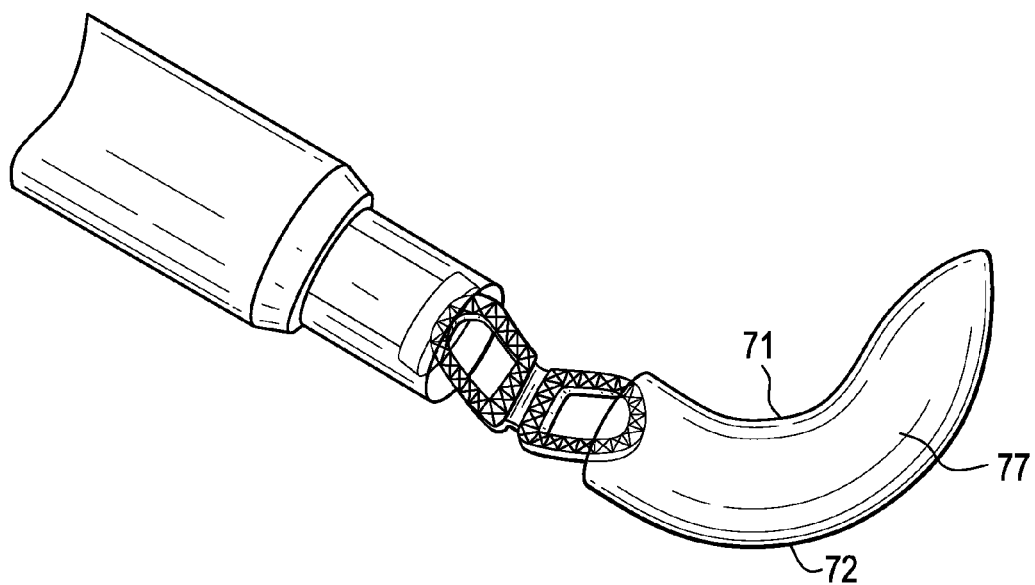
FIG. 9 discloses a distal portion of an inserter of the present invention having a modular expanding sheath tip.

In some embodiments, and now referring to FIG. 9, the cage inserter can have a modular expanding tip 77. The distal tip of the bulleted sheath can be modular and be attached to the proximal portion of the sheath. The modular component can be prepackaged sterile and marketed with the matching cage size contained within to minimize over-distraction. The entire inserter can also be polymeric and/or disposable.

Figure 10A:
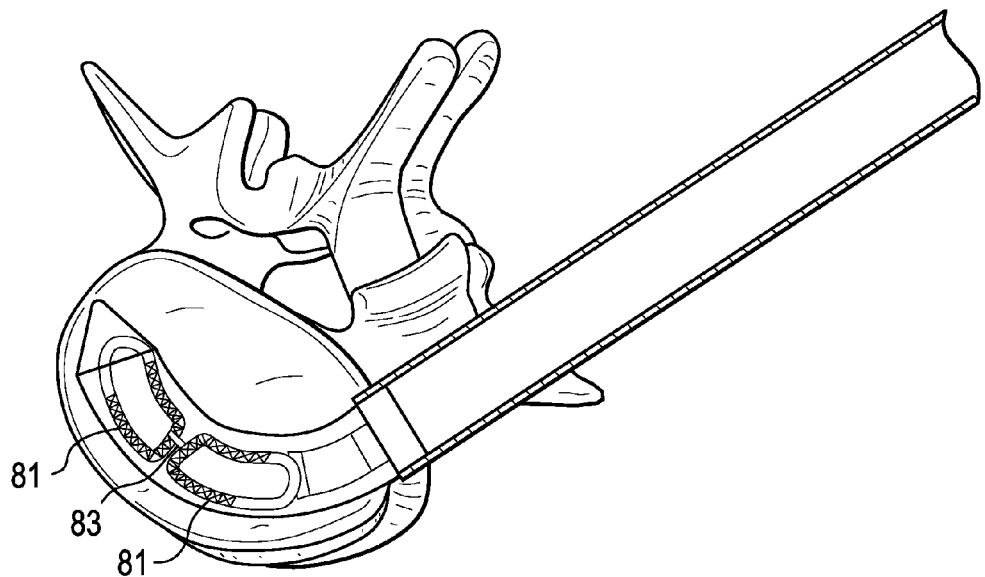
FIGS. 10A-10B disclose the insertion of multi-component cages with the inserter of the present invention.
Figure 10B:
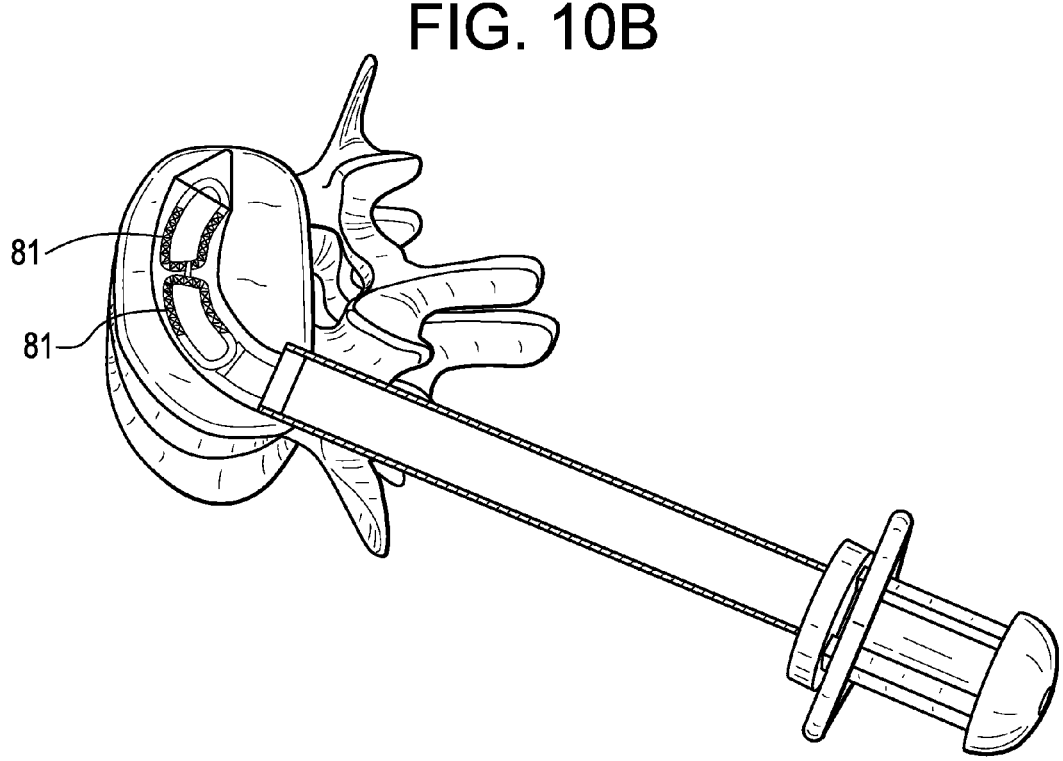

In some embodiments, and now referring to FIGS. 10 A and B, multiple cages 81 may be deployed. A plurality of curved or straight cages (or a combination of curved and straight cages) of a size smaller than a standard cage can be inserted either in succession or simultaneously. In some embodiments thereof, multiple cages can be connected to each other by a cable 83 to provide a more stable construct.

Figure 11A:
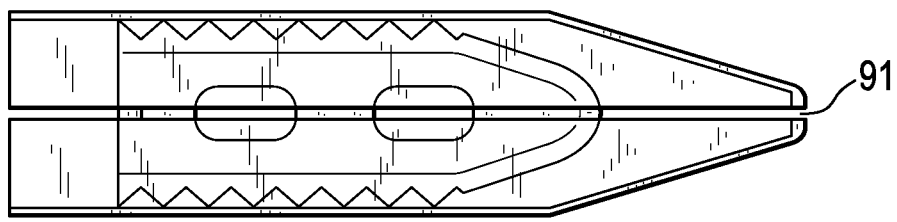
FIGS. 11A-11C disclose a distal portion of an inserter of the present invention fitted with various slit sheaths.
Figure 11B:
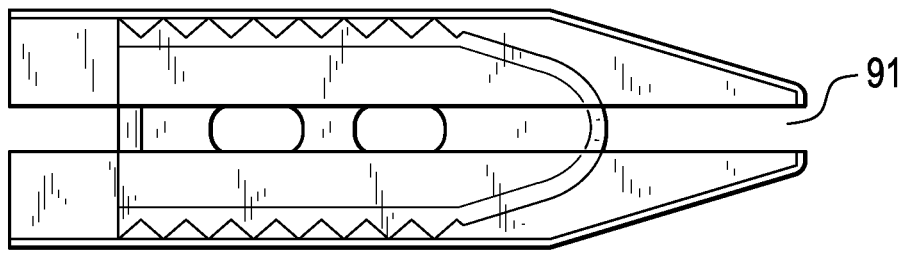
Figure 11C:
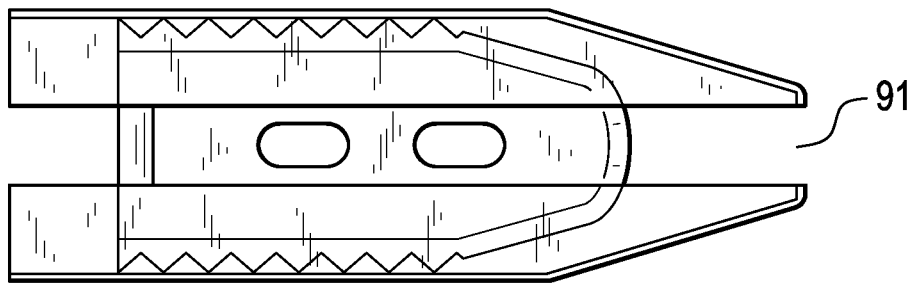

In some embodiments, and now referring to FIGS. 11A-C, the split sheath comprises a longitudinal gap 91 between sheath portions (i.e., the sheath portions do not contact each other). This gap allows for different cage heights to be handled by the same sheath component, thereby reducing the number of potential instruments in the set.

Figure 12A:
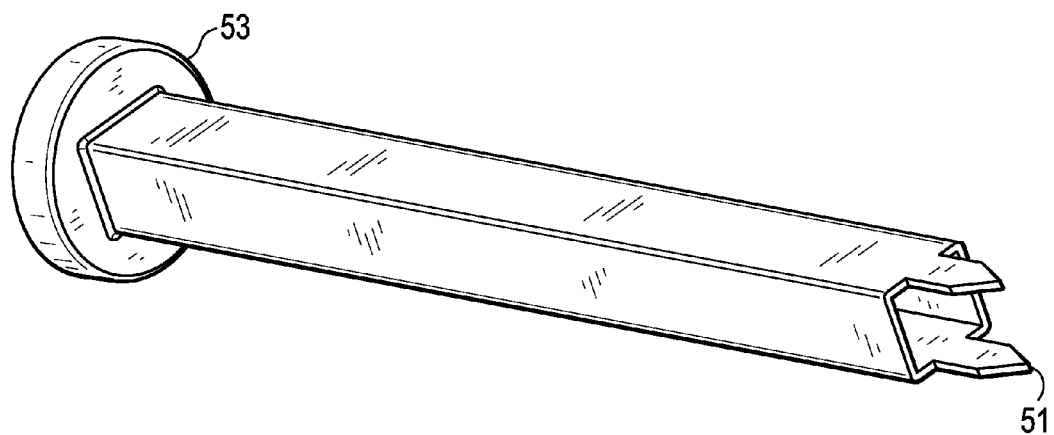
FIG. 12A discloses a docking port component of the present invention having distally extending securement teeth.
Figure 12B:
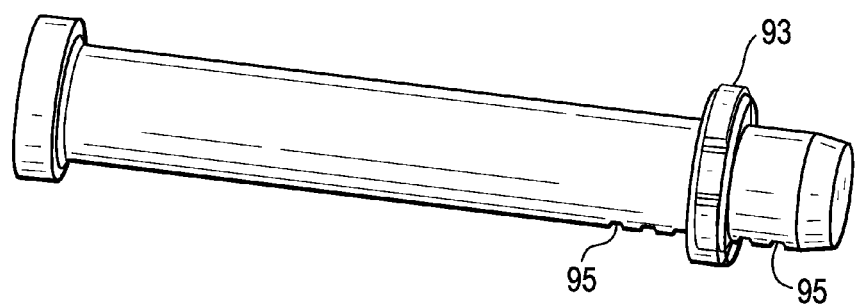
FIG. 12B discloses a docking port component of the present invention having a distally located adjustable collar.

In some embodiments, and now referring to FIGS. 12A-B, the docking port could have multiple means for attachment, such as teeth, to provide security in between or onto the vertebral bodies. In some embodiments, and now referring to FIG. 12A the docking port can have one or more tongs or spikes 51 extending distally from its distal end portion to assist in holding position upon the vertebral bodies or within the disc. Typically, the docking port also has a proximal handle 53

Now referring to FIG. 12B, the docking port could also include an adjustable collar 93 and incremental adjustment grooves 95. These components could be used to both dock onto the vertebral bodies and control the depth to which the instrument is introduced into the disc space.

Typically, the inserter of the present invention can be made out of any material commonly used in medical instruments. The cage insertion instrument can be made available in a sterile version with preassembled cage and graft, or in a reusable version. If the inserter is designed to be reusable, then it is preferred that all of its components be made of stainless steel. If the inserter is designed to be disposable, then it is preferred that at least some of the components be made of plastic. Preferably, at least one component of the inserter is sterilized. More preferably, each component is sterilized.

The intervertebral fusion cage of the present invention may be manufactured from any biocompatible material commonly used in interbody fusion procedures. In some embodiments, the cage is made from a composite comprising 40-99% polyarylethyl ketone PAEK, and 1-60% carbon fiber. Such a cage is radiolucent. Preferably, the polyarylethyl ketone PAEK is selected from the group consisting of polyetherether ketone PEEK, polyether ketone ketone PEKK, polyether ketone ether ketone ketone PEKEKK, and polyether ketone PEK. Preferably, cage is made from woven, long carbon fiber laminates. Preferably, the PAEK and carbon fiber are homogeneously mixed. Preferably, the composite consists essentially of PAEK and carbon fiber. Preferably, the composite comprises 60-80 wt % PAEK and 20-40 wt % carbon fiber, more preferably 65-75 wt % PAEK and 25-35 wt % carbon fiber. In some embodiments, the cage is made from materials used in carbon fibers cages marketed by DePuy Spine, Raynham, Mass., USA. In some embodiments, the composite is PEEK-OPTIMA™, available from Invibio of Greenville, N.C.

In other embodiments, the cage is made from a metal such as titanium alloy, such as Ti-6Al-4V. In other embodiments, the cage is made from an allograft material. In some embodiments, the cage is made from ceramic, preferably a ceramic that can be at least partially resorbed, such as HA or TCP. In other embodiments, the ceramic comprises an oxide such as either alumina or zirconia. In some embodiments, the cage is made from a polymer, preferably a polymer that can be at least partially resorbed, such as PLA or PLG.

In preferred embodiments, the cage is provided in a sterile form.

We claim:

1. An assembly comprising:
a) an intervertebral fusion cage having a leading end, a trailing end, an upper face having teeth and a lower face having teeth, and
b) an inserter comprising a cannulated sheath having a plurality of flexible sheath portions extending distally therefrom,
wherein a first sheath portion has an inner portion bearing against the teeth of the lower face of the cage,
wherein a second sheath portion has an inner portion bearing against the teeth of the upper face of the cage, and
wherein the sheath contains bone graft, at least a first portion of the bone graft is located within the cage, and at least a second portion of the bone graft is located outside of the cage but is contained by the first and second sheath portions.

2. The assembly of claim 1 wherein the sheath is located at a distal end of the inserter.

3. The assembly of claim 1 wherein the inserter further comprises a docking port having a bore therethrough, wherein the cannulated sheath is slidingly received in the docking port.

4. The assembly of claim 3 wherein the docking port has a proximal handle.

5. The assembly of claim 3 wherein the docking port has teeth for seating into or unto the vertebral bodies.

6. The assembly of claim 1 wherein the cage comprises PEEK.

7. The assembly of claim 1 wherein the cage comprises carbon fiber.

8. The assembly of claim 1 wherein the cage comprises PEEK and carbon fiber.

9. The assembly of claim 1 wherein the upper and lower faces of the cage comprise a plurality of teeth.

10. The assembly of claim 1 wherein the cage has a substantially rectangular cross-section and the sheath has a substantially corresponding substantially rectangular cross-section.

11. The assembly of claim 1 wherein the sheath comprises distal sheath leaves.

12. The assembly of claim 1 wherein the sheath comprises distal sheath quarter leaves.

13. The assembly of claim 1 wherein the sheath portions form a substantially conical sheath shape distally.

14. The assembly of claim 1 wherein the sheath portions form a distal bullet tip.

15. The assembly of claim 1 wherein the sheath portions form a substantially tubular sheath shape proximally.

16. The assembly of claim 1 wherein the sheath is curved.

17. The assembly of claim 1 wherein the sheath comprises a superelastic shape memory material.

18. The assembly of claim 1 wherein the sheath has a tensioning cable attached thereto.

19. The assembly of claim 1 wherein the sheath is modular.

20. The assembly of claim 1 wherein the cage comprises a plurality of components.

21. The assembly of claim 1 wherein the sheath leaves do not contact each other.

22. A method of inserting a fusion cage into a disc space bounded by a pair of vertebral endplates, comprising the steps of:
a) selecting the assembly of claim 1;
b) inserting the distal sheath portions of the assembly into the disc space so that the cage is within the disc space,
c) retracting the sheath from the disc space, thereby engaging the cage with the vertebral endplates.

* * * * *